United States Patent [19]

Martinez

[11] Patent Number: 4,652,255
[45] Date of Patent: Mar. 24, 1987

[54] IRRIGATING AND ASPIRATING HANDPIECE FOR USE IN OPHTHALMIC SURGERY

[76] Inventor: Miguel Martinez, 2202 Apricot, Irvine, Calif. 92714

[21] Appl. No.: 546,417

[22] Filed: Oct. 28, 1983

[51] Int. Cl.$^4$ .............................................. A61M 1/00
[52] U.S. Cl. ........................................ 604/27; 604/43
[58] Field of Search ................................... 604/27–35, 604/43, 45, 22

[56] References Cited

U.S. PATENT DOCUMENTS

| | | | |
|---|---|---|---|
| 4,007,742 | 2/1977 | Banko | 604/31 |
| 4,011,869 | 3/1977 | Seiler, Jr. | 604/22 |
| 4,014,333 | 3/1977 | McIntyre | 604/43 |
| 4,224,943 | 9/1980 | Johnson et al. | 604/28 |
| 4,519,385 | 5/1985 | Atkinson | 604/27 |

Primary Examiner—C. Fred Rosenbaum
Assistant Examiner—J. L. Kruter

[57] ABSTRACT

An irrigating and aspirating handpiece for use in ophthalmic surgery includes a tubular body having a flexible irrigating sleeve mounted on a distal end thereof, a rigid tubular aspirating tip member mounted in a tip support insert disposed in the distal end of the body and extending through the irrigating sleeve, a length of flexible irrigating tubing connected with a coupling mounted on the proximal end of the body for supplying irrigating fluid through the body, a passage in the tip insert member and the irrigating sleeve to exit at a port in the distal end of the irrigating sleeve, and a length of flexible aspirating tubing extending within the irrigating tubing and connected with the proximal end of the aspirating tip member within the body for aspirating material entering through a port in the distal end of the aspirating tip member. The irrigating and aspirating handpiece has a slim, cylindrical configuration to facilitate manipulation by a surgeon with the concentric irrigating and aspirating tubings producing no branch obstructions, and the irrigating and aspirating handpiece is constructed of a minimal number of parts easily produced and assembled to permit the handpiece to be economically disposable.

10 Claims, 9 Drawing Figures

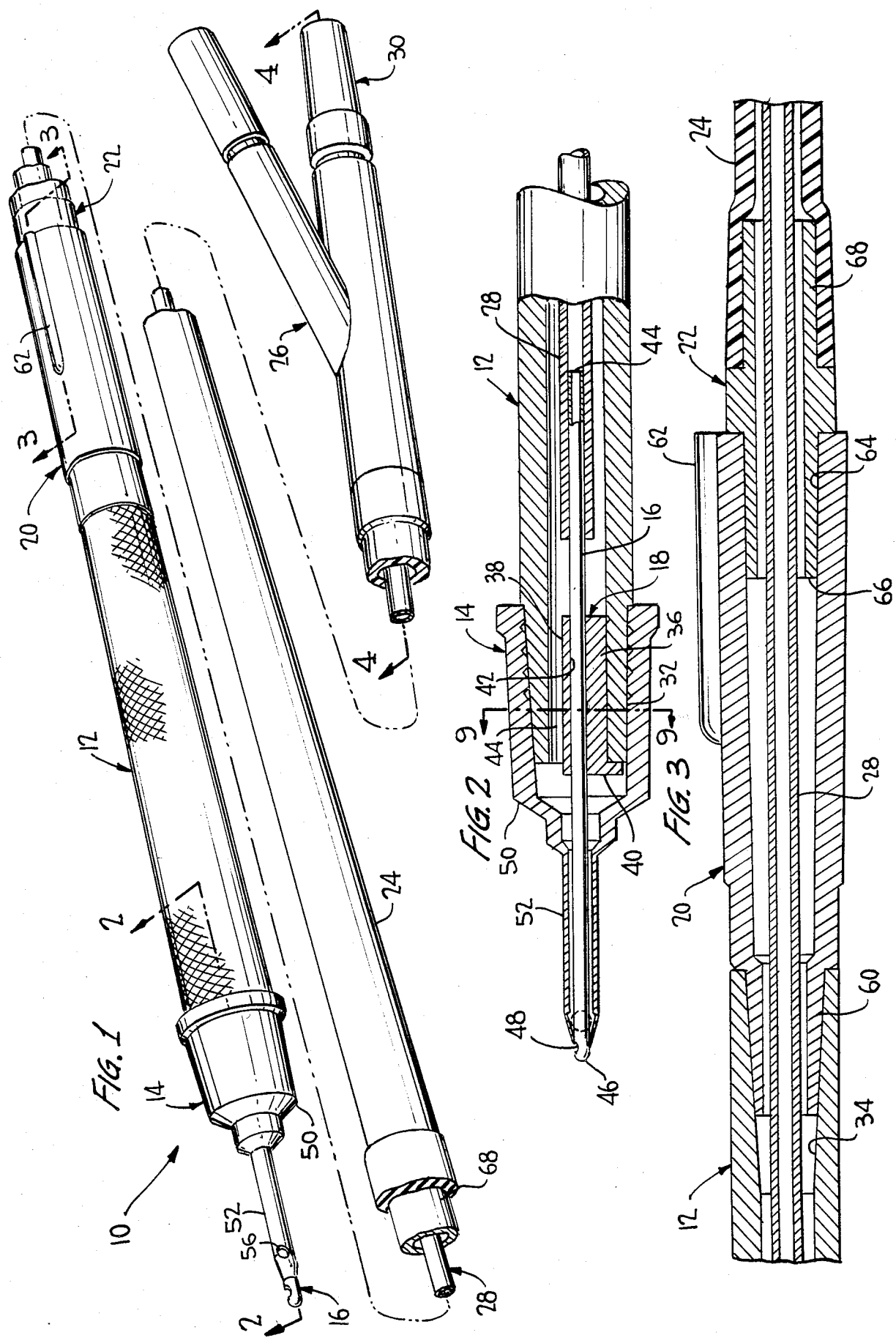

IRRIGATING AND ASPIRATING HANDPIECE FOR USE IN OPHTHALMIC SURGERY

BACKGROUND OF THE INVENTION

1. Field of the Invention

The present invention pertains to devices for use in ophthalmic surgery and, more particularly, to a disposable irrigating and aspirating handpiece for use in ophthalmic surgery.

2. Discussion of the Prior Art

Devices for aspirating and irrigating are commonly used by ophthalmic surgeons during surgical operations in the eye, and there have been many attempts to produce irrigating and aspirating instruments that can be operated by the surgeon without assistance. U.S. Pat. No. 4,014,333 to McIntyre is exemplary of prior art instruments for aspirating and irrigating during ophthalmic surgery utilizing rigid inner and outer cannulae, the inner cannula being connected with a syringe to be telescopically disposed within the outer cannula and a branch extending transversely from a connector mounting the outer cannula. Some of the disadvantages of prior art irrigating and aspirating instruments are that they are not light and configured to facilitate manipulation by the surgeon, they have protrusions interfering with the surgeon's grip and they are relatively complex in structure and assembly rendering them not economically disposable. There is a need for an economically disposable irrigating and aspirating handpiece such that the handpiece can be provided along with other materials required for a surgical operation in a sterilized package or kit, there being therefore no requirement to sterilize or disassemble the irrigating and aspirating handpiece.

SUMMARY OF THE INVENTION

Accordingly, it is a primary object of the present invention to overcome the above mentioned disadvantages of the prior art by providing an economically disposable irrigating and aspirating handpiece having a size and configuration to facilitate manipulation by a surgeon.

Another object of the present invention is to provide coaxial irrigating and aspirating flow from the end of the body of a handpiece to be gripped by a surgeon for use in ophthalmic surgery.

A further object of the present invention is to construct an economically disposable irrigating and aspirating handpiece utilizing a tubular body having a tip support insert in a distal end supporting a rigid tubular aspirating tip member and a coupling in a proximal end to receive lengths of flexible irrigating and aspirating tubing.

Some of the advantages of the present invention over the prior art are that the irrigating and aspirating handpiece of the present invention has a slim, pencil-like configuration to be easily grasped and manipulated by a surgeon, the handpiece is light in weight, the handpiece has all tubing connections extending concentrically from the end, and the handpiece is simply constructed and assembled to be economically disposable.

The present invention is generally characterized in an irrigating and aspirating handpiece for use in ophthalmic surgery including a tubular body having a distal end and a proximal end, a tip support insert disposed in the distal end of the body having an axial bore therethrough aligned with the axis of the body and a portion forming a passage therethrough communicating with the interior of the body, a irrigating sleeve having a port in a distal end thereof and a hub mounted on the distal end of the body, a rigid tubular aspirating tip member extending through the irrigating sleeve and supported in the axial bore in the tip support insert, the aspirating tip member having a distal end protruding from the irrigating sleeve having a port therein and an open proximal end disposed within the body, coupling means mounted on the proximal end of the body, a length of flexible irrigating tubing connected with the coupling means for supplying irrigating fluid through the body, the passage in the tip insert member and the irrigating sleeve to exit at the port in the distal end of the irrigating sleeve, and a length of flexible aspirating tubing extending through the irrigating tubing and connected with the proximal end of the aspirating tip member within the body for aspirating material entering through the port in the distal end of the aspirating tip member, the aspirating tubing having an outer diameter less than the inner diameter of the irrigating tubing to permit flow of irrigating fluid through the irrigating tubing.

Other objects and advantages of the present invention will become apparent from the following description of the preferred embodiment taken in conjunction with the drawings.

BRIEF DESCRIPTION OF THE DRAWINGS

FIG. 1 is a disjointed perspective view of an irrigating and aspirating handpiece according to the present invention.

FIG. 2 is a section taken along line 2—2 of FIG. 1.

FIG. 3 is a section taken along line 3—3 of FIG. 1.

DESCRIPTION OF THE PREFERRED EMBODIMENT

Figure 4:
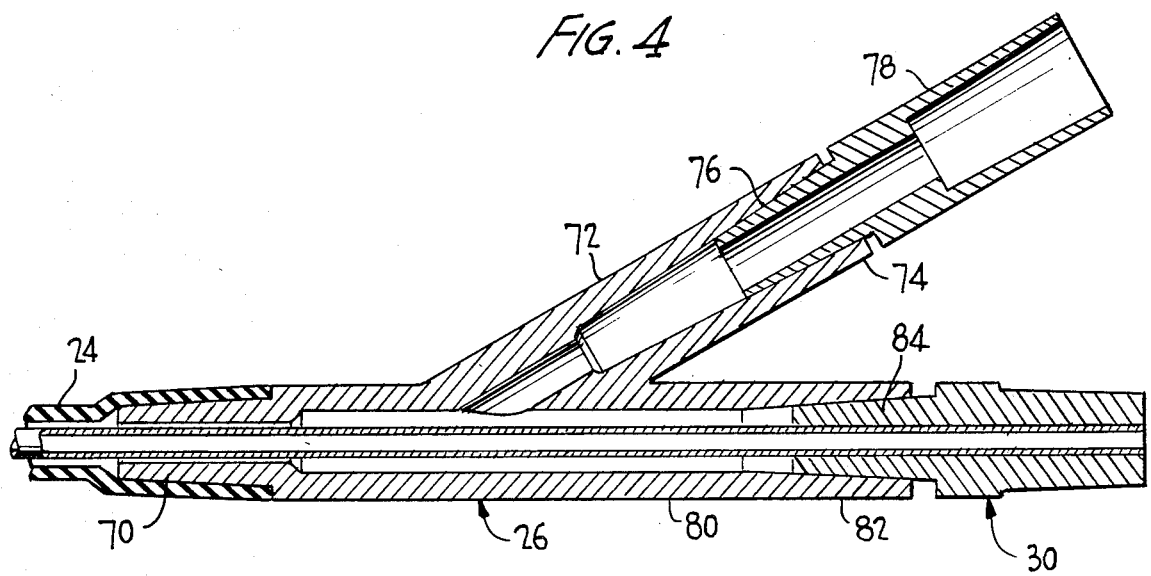
FIG. 4 is a section taken along line 4—4 of FIG. 1.

An irrigating and aspirating handpiece 10 for use in ophthalmic surgery according to the present invention is illustrated in FIG. 1 and includes as basic components a cylindrical tubular body 12, a flexible irrigating sleeve 14, a rigid tubular aspirating tip member 16 supported in a tip insert 18 in the body, a male/female coupling adapter 20 connected with the body, a male/male coupling adapter 22 connected with coupling adapter 20, a length of flexible irrigating tubing 24 connected with coupling adapter 22 and a Y-connector 26, and a length of flexible aspirating tubing 28 connected with the aspirating tip member and a coupling adapter 30 mounted on the Y-connector.

Figure 8:
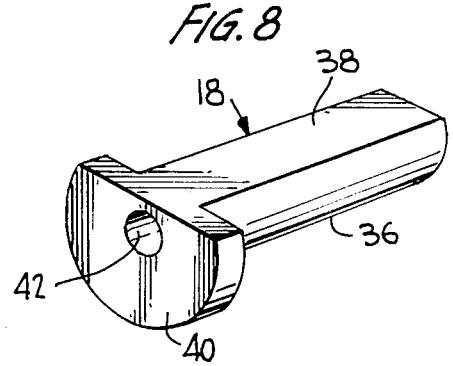
FIG. 8 is a perspective view of the tip support insert of the irrigating and aspirating handpiece of the present invention.
Figure 9:
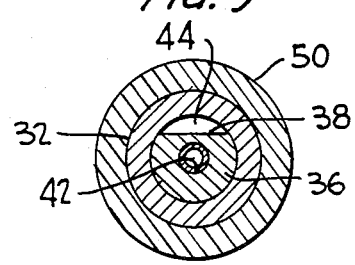
FIG. 9 is a section taken along 9—9 of FIG. 2.

The tubular body 12 is preferably made of aluminum tubing having a diameter of 0.25 inches and a length of 2.7 inches with a knurled outer surface. The distal end 32 of the body has a Luer-tapered outer surface, as shown in FIG. 2, and the proximal end 34 of the body has a Luer-tapered inner surface, as shown in FIG. 3. Tip support insert 18 is preferably made of plastic and has a partially conical stem 36 with a flat portion 38 and a head 40, as shown in FIGS. 2 and 8. The stem 36 is received in the proximal end of body 12 with a force fit, and tip support insert 18 has an axial bore 42 therethrough aligned with the axis of the body. The flat portion 38 forms a passage 44 through the tip support insert communicating with the interior of the body. The aspirating tip member 16 is preferably made of 19 gauge stainless steel and is received in axial bore 42 with a force fit to be rigidly supported in the body in alignment with the axis thereof with the proximal end 44 of the aspirating tip member disposed within the interior of the body. The aspirating tip member has a rounded, closed distal end 46 with a port 48 in the sidewall thereat.

Figure 5:
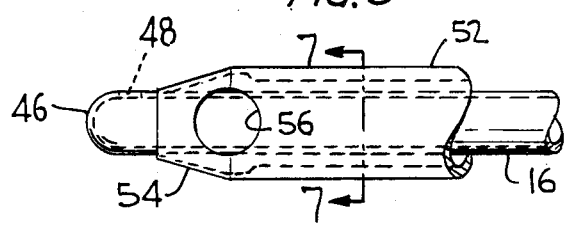
FIG. 5 is a broken plan view of the tip of the irrigating and aspirating handpiece of the present invention.
Figure 7:
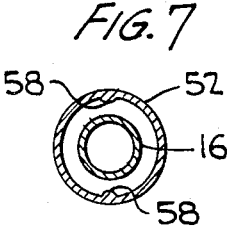
FIG. 7 is a section taken along line 7—7 of FIG. 5.
Figure 6:
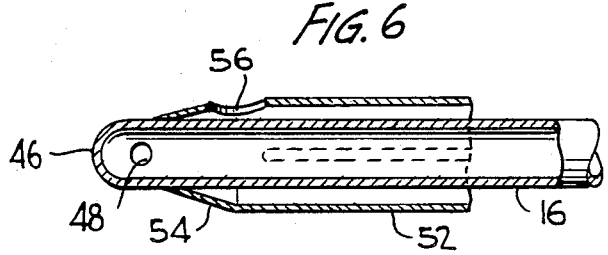
FIG. 6 is a broken section of the tip of the irrigating and aspirating handpiece of the present invention.

The irrigating sleeve 14 is preferably made of a flexible soft plastic and has a hub 50 mounted on the tapered proximal end 32 of the body and a tubular tip 52 extending around but spaced from aspirating tip member 16 terminating at a tapered distal end 54 engaging the aspirating tip member at a position so as not to cover port 48, as shown in FIGS. 5 and 6. An irrigating port 56 is disposed in irrigating sleeve 14 adjacent tapered end 54, and longitudinal ribs 58 extend along the inner surface of sleeve tip 52, as shown in FIG. 7, to prevent the sleeve tip from collapsing around the aspirating tip member to prevent flow through the annular space therebetween.

Male/female coupling adapter 20 is preferably made of plastic and has an externally Luer-tapered male member 60 received in the proximal end 34 of body 12, a longitudinal rib 62 along its outer surface and a female end 64 receiving a male member 66 of male/male coupling adapter 22 which is preferably made of plastic. The other male member 68 of coupling adapter 22 is received in the end of irrigating tubing 24 which is preferably made of transparent polyethylene and has a substantial length on the order of 12 inches, the irrigating tubing receiving at its opposite end a tapered male member at a common port 70 of Y-connector 26, as shown in FIG. 4. The Y-connector has a branch 72 terminating at an irrigating inlet 74 receiving a male member 76 of a male/female coupling adapter 78 and an in-line portion 80 terminating at an aspirating outlet 82 receiving a male member of coupling adapter 30. Aspirating tubing 28 is preferably made of transparent polyethylene having a length on the order of 15 inches, one end of the aspirating tubing being received in an axial bore in coupling adapter 30 at the aspirating outlet of Y-connector 26 and the other end receiving the proximal end 44 of aspirating tip member 16 in the interior of body 12. The aspirating tubing extends through the irrigating tubing and has an outer diameter less than the inner diameter of the irrigating tubing to permit flow of irrigating fluid through the space between the tubings.

From the above, it will be appreciated that assembly of the irrigating and aspirating handpiece 10 is simplified by force fitting of the various components together while the components are not intricate and function together to provide unobstructed coaxial flow paths for irrigation and aspiration.

In use, the configuration and size of the irrigating and aspirating handpiece 10 permits a surgeon to grip the body 12 in pencil-like fashion for use in ophthalmic surgery with no connections interfering with the surgeon's grip. A suitable irrigating fluid is supplied under pressure to coupling adapter 78 at the Y-connector, and the irrigating fluid flows through branch 72 and the space between the irrigating and aspirating tubings to coupling adapter 22 where the irrigating fluid flows through body 12, passage 44 and the space between sleeve tip 52 and aspirating tip member 16 to exit at port 56 to the surgical site. The aspiration flow path extends from port 48 through the aspirating tip member 16 and the aspiration tubing to coupling adapter 30 at the Y-connector which can be connected with any suitable source of suction.

The concentric irrigating and aspirating tubings produce no branch obstructions to interfere with gripping of the irrigating and aspirating handpiece by the surgeon and also facilitate assembly of the handpiece and construction without intricate or complex components. Additionally, the use of transparent tubings facilitates visual detection of flow by the surgeon.

Inasmuch as the present invention is subject to many variations, modifications and the changes in detail, it is intended that all subject matter discussed above or shown in the accompanying drawings be interpreted as illustrative and not in a limiting sense.

What is claimed is:

1. An irrigating and aspirating handpiece for use in ophthalmic surgery comprising a tubular body having a distal end and a proximal end and having a length to permit said body to be gripped in pencil-like fashion for use in ophthalmic surgery;

a tip support insert disposed in said distal end of said body having an axial bore therethrough aligned with the axis of said body and a portion forming in said distal end of said body a passage therethrough communicating with the interior of said body;

an irrigating sleeve having a port in a distal end thereof and a hub mounted on said distal end of said body;

a stationary rigid tubular aspirating tip member extending through said irrigating sleeve and rigidly supported in said axial bore of said tip support insert, said aspirating tip member having a distal end protruding from said distal end of said irrigating sleeve having a port therein and an open proximal end disposed within said body;

coupling means mounted on said proximal end of said body;

a length of flexible irrigating tubing connected with said coupling means for supplying irrigating fluid through said body, said passage in said tip support insert and said irrigating sleeve to exit at said port in said distal end of said irrigating sleeve; and a length of flexible aspirating tubing extending through said irrigating tubing and connected with said proximal end of said aspirating tip member within said body for aspirating material entering through said port in said distal end of said aspirating tip member, said aspirating tubing having an outer diameter less than the inner diameter of said irrigating tubing to permit flow of irrigating fluid through said irrigating tubing and provide concentric paths for irrigating and aspirating flow.

2. An irrigating and aspirating handpiece as recited in claim 1 wherein said irrigating and aspirating tubings are transparent.

3. An irrigating and aspirating handpiece as recited in claim 1 and further comprising a Y-connector having a common port communicating with an aspirating outlet and an irrigating inlet, said irrigating tubing being connected with said common port for receiving irrigating fluid supplied to said irrigating inlet, and an adapter disposed in said aspirating outlet to block flow of irrigating fluid therethrough and having an axial bore therethrough receiving said aspirating tubing.

4. An irrigating and aspirating handpiece as recited in claim 1 wherein said tubular body is made of a rigid material, said tip support insert is made of plastic and disposed in said distal end of said body with a force fit and said aspirating tip member is supported in said axial bore in said tip support insert with a force fit.

5. An irrigating and aspirating handpiece as recited in claim 4 wherein said coupling means includes a coupling adapter made of plastic having a male member received in said proximal end of said body with a force fit.

6. An irrigating and aspirating handpiece as recited in claim 5 wherein said coupling adapter has a female end and said coupling means further includes a second coupling adapter made of plastic having a first male member received in said female end of said first mentioned coupling adapter with a force fit and a second male member received in said irrigating tubing.

7. An irrigating and aspirating handpiece for use in ophthalmic surgery comprising
a tubular body having a distan end and a proximal end;
a tip support insert disposed in said distal end of said body having a stem engaging said distal end of said body, an axial bore through said stem aligned with the axis of said body and a flat portion along said stem forming a passage therethrough communicating with the interior of said body;
an irrigating sleeve having a port in a distal end thereof and a hub mounted on said distal end of said body;
a rigid tubular aspirating tip member extending through said irrigating sleeve and supported in said axial bore in said tip support insert, said aspirating tip member having a distal end protruding from said irrigating sleeve having a port therein and an open proximal end disposed within said body;
coupling means mounted on said proximal end of said body;
a length of flexible irrigating tubing connected with said coupling means for supplying irrigating fluid through said body, said passage in said tip support insert and said irrigating sleeve to exit at said port in said distal end of said irrigating sleeve; and
a length of flexible aspirating tubing extending through said irrigating tubing and connected with said proximal end of said aspirating tip member within said body for aspirating material entering through said port in said distal end of said aspirating tip member, said aspirating tubing having an outer diameter less than the inner diameter of said irrigating tubing to permit flow of irrigating fluid through said irrigating tubing.

8. An irrigating and aspirating handpiece as recited in claim 7 wherein said irrigating and aspirating tubings are transparent.

9. An irrigating and aspirating handpiece as recited in claim 8 and further comprising a Y-connector having a common port communicating with an aspirating outlet and an irrigating inlet, said irrigating tubing being connected with said common port for receiving irrigating fluid supplied to said irrigating inlet, and an adapter disposed in said aspirating outlet to block flow of irrigating fluid therethrough and having an axial bore therethrough receiving said aspirating tubing.

10. An irrigating and aspirating handpiece as recited in claim 9 wherein said Y-connector is made of transparent plastic.

* * * * *